United States Patent [19]

Suzuki et al.

[11] Patent Number: 5,275,938
[45] Date of Patent: Jan. 4, 1994

[54] PROCESS FOR PRODUCING LEUCANICIDIN

[75] Inventors: Akinori Suzuki; Akira Isogai, both of Chiba; Shogo Matsumoto; Shohei Sakuta, both of Tokyo; Mitsuo Ogura, Kamakura; Hruo Seto, Hachioji; Kazuo Furihata, Tokyo, all of Japan

[73] Assignee: Nisshin Flour Milling Co., Ltd., Japan

[21] Appl. No.: 999,802

[22] Filed: Dec. 28, 1992

Related U.S. Application Data

[60] Continuation of Ser. No. 679,175, Mar. 27, 1991, abandoned, which is a continuation of Ser. No. 364,553, Jun. 8, 1989, abandoned, which is a continuation of Ser. No. 87,518, Aug. 20, 1987, abandoned, which is a division of Ser. No. 694,263, Jan. 24, 1985, Pat. No. 4,730,039.

[30] Foreign Application Priority Data

Mar. 9, 1984 [JP] Japan .................................. 59-43815

[51] Int. Cl.$^5$ .................. C12P 19/60; C12P 19/62; C12P 19/44; C12N 1/20
[52] U.S. Cl. ........................................ 435/75; 435/76; 435/74; 435/886; 435/253.5
[58] Field of Search .................... 435/75, 74, 897, 902, 435/886, 253.5

[56] References Cited

U.S. PATENT DOCUMENTS 4,022,885 5/1977 Celmer et al. ...................... 424/122
4,361,649 11/1982 Celmer et al. ...................... 435/119

OTHER PUBLICATIONS

Shimauchi et al., *J. Antibiotics* vol. 31, pp. 261-275, 1978.

*Primary Examiner*—Irene Marx
*Attorney, Agent, or Firm*—Larson and Taylor

[57] ABSTRACT

New compound, designated as leucanicidin, is now provided and is useful as insecticide. Leucanicidin is fermentatively produced by a microorganism *Streptomyces halstedii* No. 3002-14, (FEKM BP-493).

1 Claim, 3 Drawing Sheets

PROCESS FOR PRODUCING LEUCANICIDIN

This application is a continuation of application Ser. No. 07/679,175 filed Mar. 27, 1991, now abandoned, which is a continuation of application Ser. No. 07/364,553 filed Jun. 8, 1989, now abandoned, which is a continuation of application Ser. No. 07/087,518 filed Aug. 20, 1987, now abandoned, which is a divisional of application Ser. No. 06/694,263 filed Jan. 24, 1985, now U.S. Pat. No. 4,730,039.

SUMMARY OF THE INVENTION

This invention relates to a new physiologically active compound, now named leucanicidin, which is useful as an insecticide, and to a process for the production thereof.

BACKGROUND OF THE INVENTION

Many strains of the genus Streptomyces are known to be able to produce useful substances such as antibiotics which are useful as antibacterial agent, anti-tumor agent or herbicide. Some substances which are fermentatively produced by some strains of the genus Streptomyces have an activity against a certain kind of insects harmful to human beings and detrimental to the living environment. However, there is still further a need for a more effective agents useful for control of pests.

An object of this invention is to provide a new compound which is useful as an insecticide. A further object of this invention is to provide a process for the fermentative production of such new compound.

DETAILED DESCRIPTION OF THE INVENTION

We, the present inventors have made extensively research in an attempt to produce and obtain new physiologically active compounds, particularly useful for control of insects harmful to human beings. As a result, we, the present inventors have found that when a new strain of actinomycetes which was isolated by us from a soil sample collected from the ground in Tsu City, Mie Prefecture, Japan and which may be considered to belong to Streptomyces halstedii, is cultivated in a culture medium under aerobic conditions, there is produced and accumulated in the culture medium a new substance which shows an activity inhibitory to noxious and harmful insects such as armyworm (Leucania separata). We, the present inventors have now succeeded in isolating this new substance in a purified form from the culture of the Streptomyces halstedii strain. From the chemical, physical and biological studies, the isolated substance has been confirmed to be a new compound and now named as leucanicidin.

According to a first aspect of this invention, therefore, there is provided a new compound named leucanicidin. Leucanicidin may be obtained in the form of colorless crystals, as will be described in detail hereinafter, for example, by cultivating a leucanicidin-producing strain of the genus Streptomyces in a culture medium, collecting the cells of the microorganism, extracting the cells with a water-miscible organic solvent or an aqueous organic solvent, fractionating the extract by silica-gel chromatography or in any other conventional chromatographic techniques and then concentrating the active fractions containing leucanicidin, followed by crystallizing a crude product of leucanicidin from a suitable solvent.

Physico-chemical properties of leucanicidin thus obtained may be summarized as follows:
1. Molecular formula; $C_{42}H_{70}O_{13}$
2. Molecular weight; 782
3. Chemical structure;

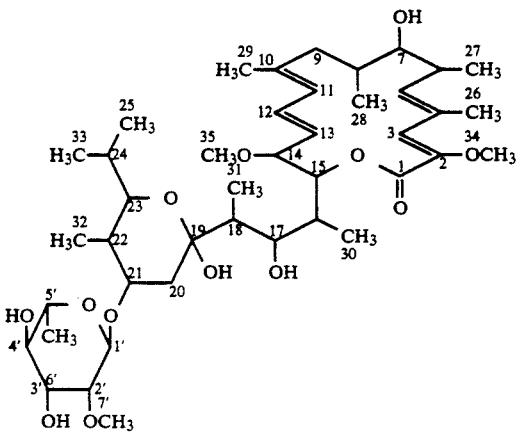

4. $(\alpha)_D^{26}$; $-47°$ (c=1.0, CHCl$_3$)
5. Melting point; 130°-132° C.
6. Elementary analysis;
   Calcd. for $C_{42}H_{70}O_{13} \cdot (4/5)CHCl_3$: C 58.52, H 8.12, O 23.68, Cl 9.68%. Found; C 58.77, H 8.02, O 23.67, Cl 9.40%.
7. Ultraviolet absorption spectrum (in methanol); As shown in FIG. 1 of the accompanying drawings. $\lambda_{max}$ MeOH: 248 nm ($\epsilon$=21000), 287 nm ($\epsilon$=9350).
8. Infrared absorption spectrum (pelleted in potassium bromide);
   As shown in FIG. 2 of the accompanying drawings. $\nu_{max}$ KBr cm$^{-1}$: 3500-3400, 1680, 1640, 1615, 1240.
9. Proton-NMR (in deutero-chloroform); As shown in FIG. 3 of the accompanying drawings.

| Position | δ (ppm) | Splitting pattern | | J (H$_z$) | | |
|---|---|---|---|---|---|---|
| 33 | 0.76 | d | 3H | 7 | | |
| 30 | 0.82 | d | 3H | 7 | | |
| 25 | 0.91 | d | 3H | 7 | | |
| 32 | 0.92 | d | 3H | 7 | | |
| 28 | 0.94 | d | 3H | 7 | | |
| 31 | 1.05 | d | 3H | 7 | | |
| 20b | 1.05 | br.t | 1H | 7 | 2 | |
| 27 | 1.07 | d | 3H | 7 | | |
| 6' | 1.29 | d | 3H | 6 | | |
| 22 | 1.44 | m | 1H | 10 | 10 | 7 |
| 7-OH | 1.54 | d | 1H | 6.5 | | |
| 18 | 1.76 | br.q | 1H | 7 | 2 | |
| 8 | 1.91 | m | 1H | 7 | 7 | 11 |
| 24 | 1.91 | m | 1H | 7 | 7 | 2 |
| 9b | 1.93 | d.d | 1H | 14 | 11 | |
| 29 | 1.93 | br.s | 3H | | | |
| 26 | 1.99 | d | 3H | 1 | | |
| 16 | 2.13 | m | 1H | 11 | 7 | 2 |
| 9a | 2.14 | br.d | 1H | 14 | 1 | |
| 3'-OH | 2.33 | d | 1H | 10 | | |
| 4'-OH | 2.33 | br.s | 1H | | | |
| 20a | 2.39 | d.d | 1H | 11 | 5 | |
| 6 | 2.54 | m | 1H | 9 | 7 | 2 |
| 35 | 3.24 | s | 3H | | | |
| 7 | 3.29 | m | 1H | 11 | 7 | 7 |
| 2' | 3.37 | d.d | 1H | 15 | 3 | |
| 4' | 3.37 | br.t | 1H | 9 | | |
| 7' | 3.47 | s | 3H | | | |
| 23 | 3.53 | d.d | 1H | 10 | 2 | |
| 34 | 3.64 | s | 3H | | | |
| 3' | 3.71 | m | 1H | 10 | 9 | 3 |
| 5' | 3.72 | d.q | 1H | 9 | 6 | |

-continued

| Position | δ (ppm) | Splitting pattern | | | J (H$_z$) | |
|---|---|---|---|---|---|---|
| 21 | 3.74 | m | 1H | 11 | 10 | 5 |
| 14 | 3.88 | t | 1H | 9 | | |
| 17 | 4.14 | m | 1H | 11 | 4 | 2 |
| 17-OH | 4.63 | d | 1H | 4 | | |
| 15 | 4.96 | d.d | 1H | 9 | 2 | |
| 1' | 5.05 | d | 1H | 1.5 | | |
| 13 | 5.16 | br.d.d. | 1H | 15 | 9 | |
| 19-OH | 5.46 | d | 1H | 2 | | |
| 5 | 5.77 | br.d | 1H | 9 | 1 | |
| 11 | 5.81 | br.d | 1H | 11 | 1 | |
| 12 | 6.51 | d.d | 1H | 15 | 11 | |
| 3 | 6.67 | br.s | 1H | | | |

10. $^{13}$C-NMR (in deutero-chloroform); As shown in FIG. 4 of the accompanying drawings.

| C-position | δ (ppm) | multi-plicity | C-position | δ (ppm) | Multi-plicity |
|---|---|---|---|---|---|
| 31 | 7.2 | q | 3' | 68.1 | d |
| 30 | 9.8 | q | 17 | 70.7 | d |
| 25 | 12.7 | q | 5' | 71.7 | d |
| 26 | 14.0 | q | 4' | 74.0 | d |
| 28 | 14.3 | q | 2' | 75.1 | d |
| 27 | 17.3 | q | 23 | 75.8 | d |
| 6' | 17.5 | q | 15 | 76.8 | d |
| 29 | 20.2 | q | 7 | 81.2 | d |
| 33 | 21.1 | q | 21 | 81.2 | d |
| 32 | 21.7 | q | 14 | 82.3 | d |
| 24 | 27.9 | d | 1' | 92.3 | d |
| 6 | 36.7 | d | 19 | 98.8 | s |
| 16 | 37.2 | d | 11 | 125.3 | d |
| 22 | 38.9 | d | 13 | 127.2 | d |
| 20 | 39.0 | t | 4 | 133.0 | s |
| 8 | 40.0 | d | 12 | 133.0 | d |
| 9 | 41.3 | t | 3 | 133.5 | d |
| 18 | 42.2 | d | 2 | 141.3 | s |
| 35 | 55.5 | q | 5 | 142.8 | d |
| 7' | 58.8 | q | 10 | 143.0 | s |
| 34 | 59.9 | q | 1 | 167.3 | s |

11. Color and Appearance of crystal; Colorless needles or plates.

12. Solubility; Soluble in chloroform, ethyl acetate, pyridine, acetone, ethanol and methanol. Insoluble in hexane and water.

13. R$_f$ values on TLC; R$_f$ value=0.43 on thin layer chromatography (on Silica gel plate, Merck No. 5715) as developed with ethyl acetate.

With reference to the accompanying drawings.

Figure 1:
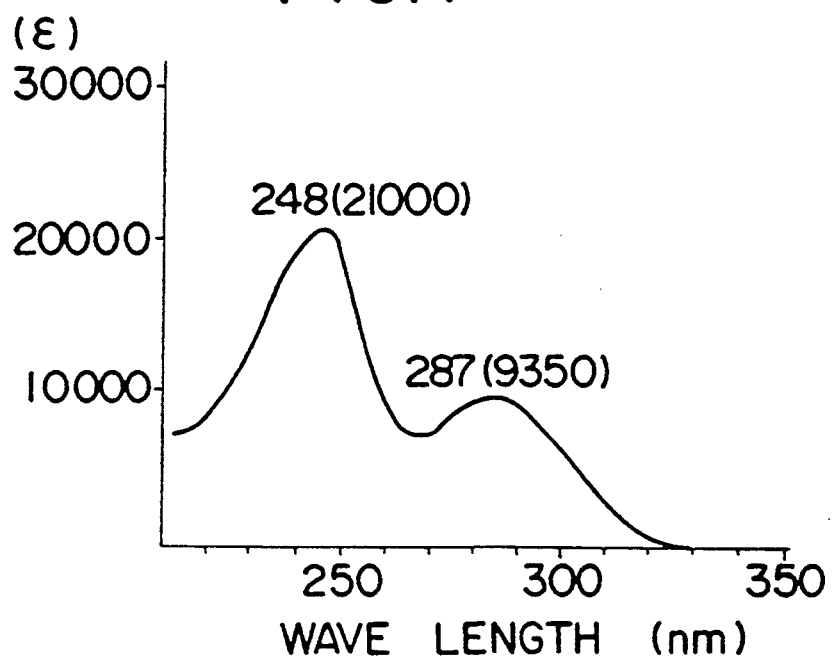
FIG. 1 shows a ultraviolet absorption spectrum of leucanicidin in methanol.
Figure 2:
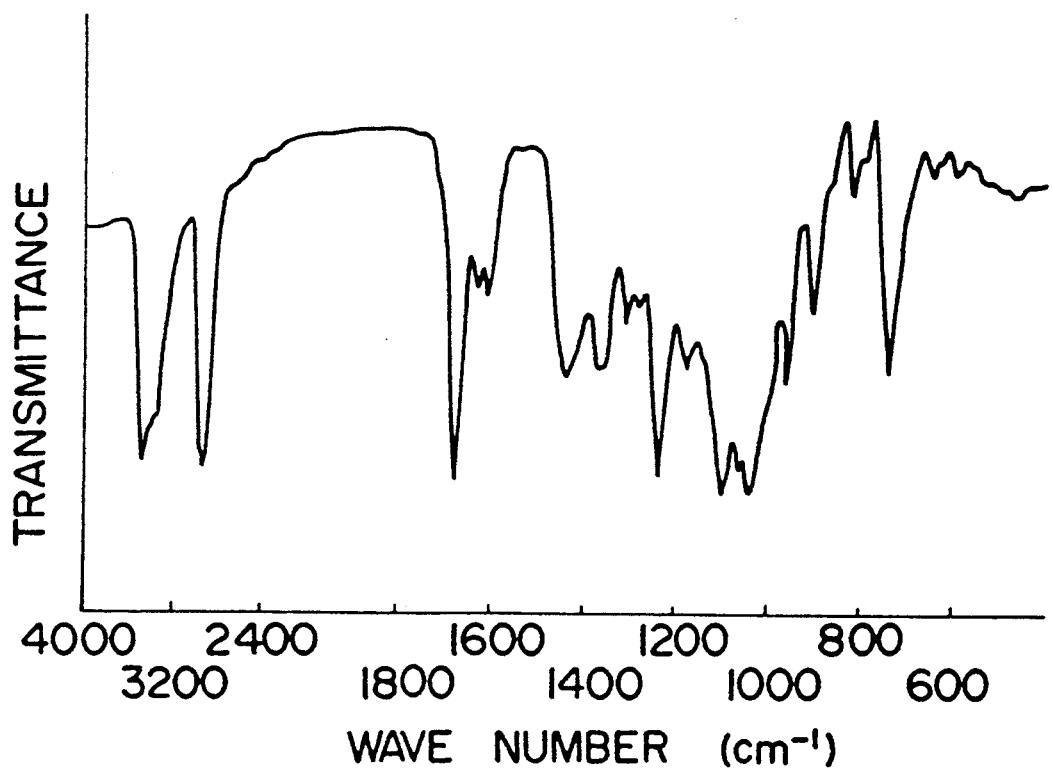
FIG. 2 shows an infrared absorption spectrum of leucanicidin pelleted in potassium bromide.
Figure 3:
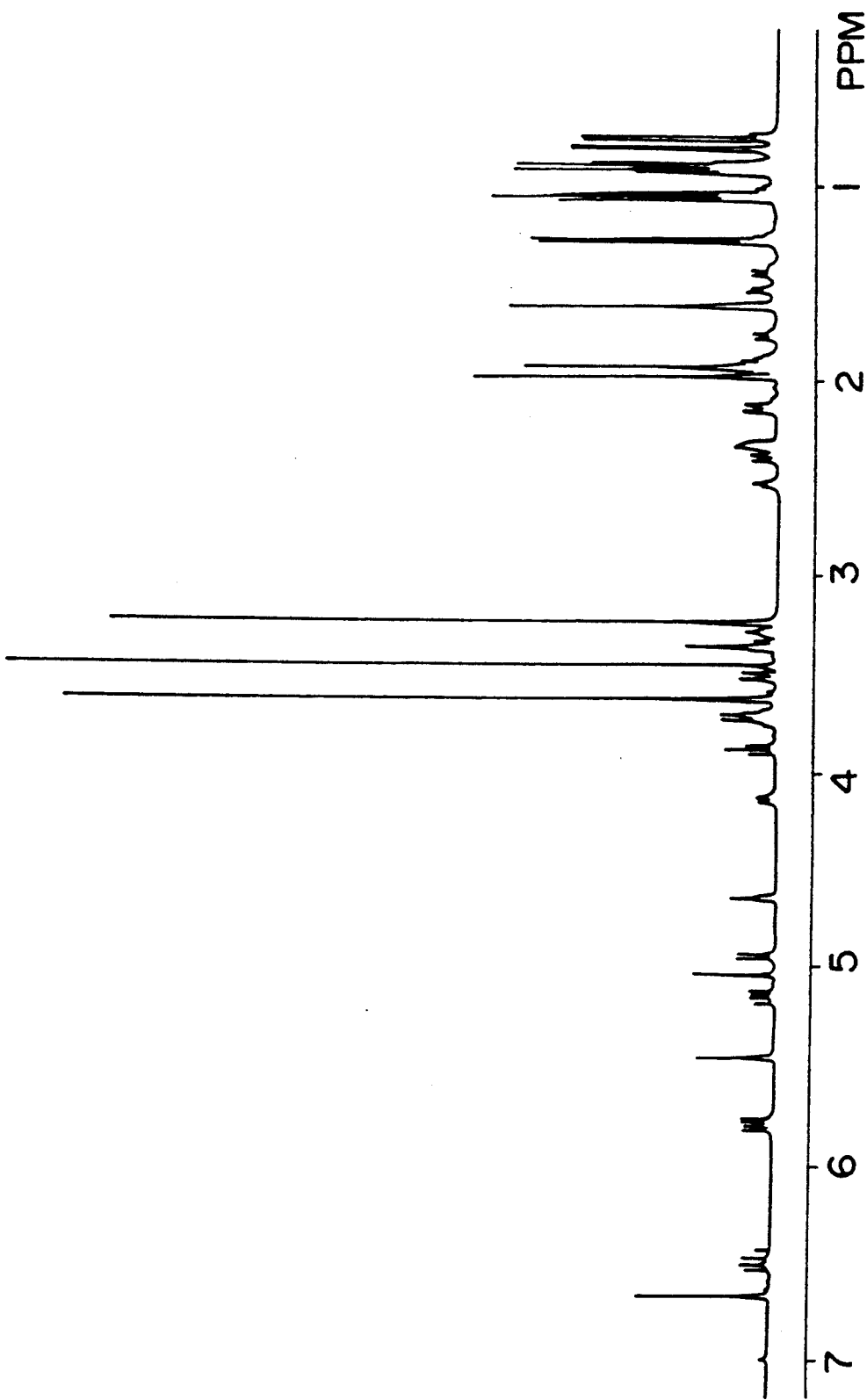
FIG. 3 shows a $^1$H-nuclear magnetic resonance spectrum of leucanicidin in deutero-chloroform.
Figure 4:
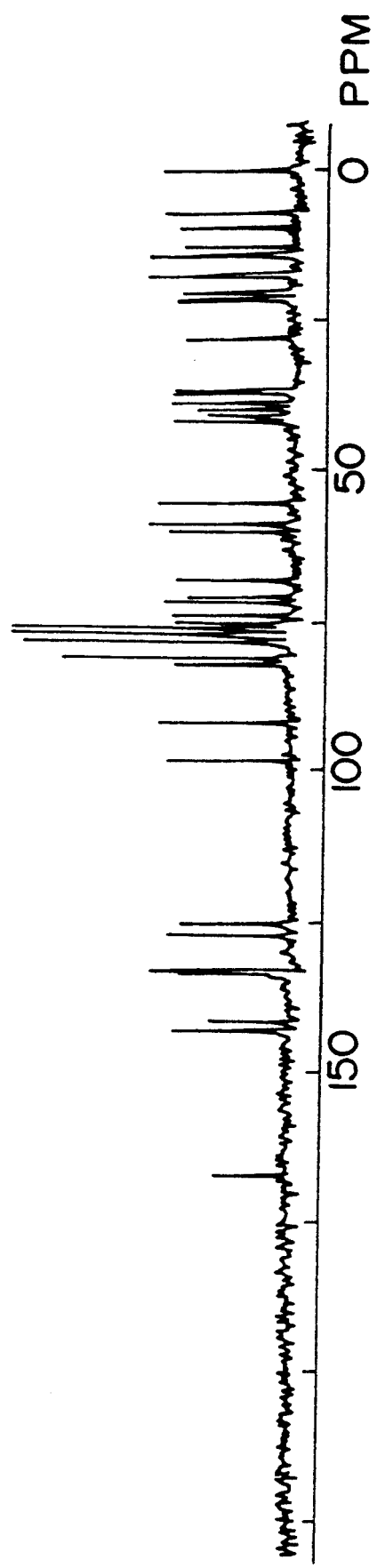
FIG. 4 shows a $^{13}$C-nuclear magnetic resonance spectrum of leucanicidin in deutero-chloroform.

The new compound of this invention, leucanicidin, either in a pure form or in a crude form, is active against noxious insects, such as armyworm (Leucania separata) infesting rice plants or vegetables. It has been found that when leucanicidin is orally given at an effective dose to larvae of armyworm, this insect is killed due to the insecticidal activity of leucanicidin. For the purpose of combatting noxious insects, a composition comprising an insecticidally effective amount of leucanicidin in association with an inert carrier for the active compound may be applied directly to insects or to the foliage of plants which have been infested with noxious insects such as armyworm, so that the insects can contact with leucanicidin or the insects can take the foliage treated with leucanicidin. The inert carrier available to this end may be liquid or solid. Liquid carrier may be an organic solvent such as aqeous methanol, aqueous ethanol, aqueous acetone and other conventional ones, and solid carrier may be conventional inorganic one such as talc, clay or organic one such as starch, wheat flour and other conventional one which may be orally taken by the insects to be combatted.

The production of leucanicidin is achieved fermentatively by cultivating a leucanicidin-producing strain of the genus Streptomyces, such as a strain of *Streptomyces halstedii*.

According to a second aspect of this invention, therefore, there is provided a process for the production of leucanicidin, which comprises cultivating a leucanicidin-producing strain of the genus Streptomyces under aerobic conditions in a culture medium containing assimilable carbon and nitrogen sources until leucanicidin is produced and accumulated in the culture, and recovering the leucanicidin from the culture.

An example of the leucanicidin-producing strain is, as described hereinbefore, a strain of the genus Streptomyces which was isolated from a soil sample collected in Tsu City, Mie Prefecture, Japan, and which was designated as *Streptomyces halstedii* No. 3002-14 and has been deposited since 29th Feb. 1984 in "Fermentation Research Institute", Agency of Industrial Science and Technology, Tukuba-gun, Ibaragi Prefecture, Japan under the deposit number FERM BP-493 according to Budapest Treaty.

*Streptomyces halstedii* No. 3002-14 has the following microbiological properties:

(1) Cultural characteristics on different culture media (incubated at 27° C.)

| Medium | Color of Colony | Reverse side of colony | Diffusible pigment in medium |
|---|---|---|---|
| Sucrose-nitrate agar | Aerial mycelium scant, powdery with brownish gray (3ig~3li)* | Thin, broaden, colorless or brownish gray | None |
| Glucose-asparagine agar | Brownish gray (3ig~4li) with sprinkled white spots | Light brownish gray~grayish yellow brown | trace of yellowish |
| Glycerine-asparagine agar | Light brownish gray to brownish gray (3fe~3ig) with sprinkled white or grayish patches | Pale yellow to pale yellowish brown | None |
| Starch-inorganic salt agar | Brownish gray (3ig) with moist black edges of colonies | Light brown to dark brown with black edges | Light brownish gray to brownish gray |
| Tyrosine agar | No aerial mycelium | Colorless to light yellow | None |
| Nutrient agar | No aerial mycelium | Colorless or light brownish gray | None |
| Yeast malt agar | Aerial mycelium scant, white | Pale yellowish orange to pale yellowish brown | None |
| Oatmeal agar | Brownish gray (3ig) | Light brownish gray to pale yellowish brown or grayish yellow | traces of light brownish gray |

-continued

| Medium | Color of Colony | Reverse side of colony | Diffusible pigment in medium |
|--------|-----------------|------------------------|------------------------------|
|        |                 |                        | brown                        |

*The color standard given in the brackets above is according to the color standard set forth in the "Color Harmony Manual" 4th edition, published by Container Corporation of America, (1950).

(2) Physiological properties (incubated at 27° C. except for the temperature for growth)

| Temperature for growth | 20~40° C. |
| Temperature for optimum growth | 27~40° C. |
| Liquefaction of gelatin | + |
| Hydrolysis of starch | + |
| Coagulation of skimmed milk | + |
| Peptonization of skimmed milk | + |
| Formation of melanoid pigment | |
| on tyrosine agar | − |
| on peptone-yeast extract-iron agar | − |
| on trypton-yeast broth | − |
| Reduction of nitrate | + |

(3) Utilization of carbon sources (incubated at 20° C.)

| L-Arabinose: | positive | (+) | i-Inositol: | negative | (−) |
| D-Xylose: | positive | (+) | L-Rhamnose: | negative | (−) |
| D-Glucose: | positive | (+) | Raffinose: | positive | (+) |
| D-Fructose: | doubtful | (±) | D-Mannitol: | negative | (−) |
| Sucrose: | doubtful | (±) | | | |

From the above observations, it is seen that the present strain No. 3002-14 is characterized by having a spore chain bearing 20~40 spores and the I type of cell wall, revealing that the present strain No. 3002-14 belongs to the genus Streptomyces. On the basis of the above-mentioned properties of the present strain No. 3002-14, this strain was compared to known species or strains of Streptomyces with reference to the description in the following literatures: Bergy's Manual of Determinative Bacteriology, 8th Edition; International Journal of Systematic Bacteriology vol. 18 No. 4. It is noted that the characteristics of the strain No. 3002-14 resembles most closely to those of *Streptomyces halstedii* ISP 5068. Although there is a slight difference in the type of spore chain and the utilization of carbon sources, the strain No. 3002-14 and *Streptomyces halstedii* ISP 5068 well coincide to each other in their properties in many points.

The strain No. 3002-14 has chains of spores which are mainly in a straight, curved (bent) or coiled form, and there is occasionally observed a closed spiral or irregular coil-like form of spore-chain, whereas *Streptomyces halstedii* ISP 5068 strain shows chains of spores which are mainly in a waved form, and occasionally in a curved or irregular coil-like form. However, Waksman describes, in the first edition, that *Streptomyces halstedii* ISP 5068 strain has a tendency to have a closed spiral of spore-chain, from which it may be presumed that the ISP 5068 strain has lost the property to form the closed spiral of spore-chain in a long time of preservation of the culture. This presumption is supported by the fact that the ISP 5068 strain has shown a depression in the spore-production and a decrease in the numbers of spore (3~10) per a chain of spore in the ISP strain. The No. 3002-14 strain as freshly prepared from the soil may be considered to have morphological characteristics which more closely resemble to those of the ISP 5068 strain described in the Waksman's first edition rather than to those of the ISP 5068 strain now available at the present time. Besides, the difference in the D-fructose utilization is not the essential factor for differentiating said two strains from each other as different two species or subspecies of Streptomyces.

From the above-mentioned identifying characteristics of the present strain No. 3002-14, this strain is designated as *Streptomyces halstedii* No. 3002-14.

The production of leucanicidin according to this invention may be performed fermentatively by aerobic cultivation of an leucanicidin-producing strain of the genus Streptomyces, for example, *Streptomyces halstedii* No. 3002-14, (FERM BP-493). The cultivation of this strain may be carried out under aerobic conditions in a medium comprising water-soluble nutrients suitable for the cultivation of ordinary actinomycetes at a temperature in a range of 20° to 37° C., preferably 25° to 30° C.

Nutrient constituents of the culture media commonly employed for cultivation of ordinary actinomycetes can be used for incubation of the leucanicidin-producing strain for the purpose of this invention. For instance, commercially available glucose, fructose, sucrose and other sugars, starch and glycerine, and the mixture thereof are useful as the carbon source. Commercially available casein, polypeptone, soybean meal, cotton seed meal, meat extract, dry yeast extract, corn steep liquor, and other organic nitrogen compounds, ammonium sulfate, ammonium chloride and other inorganic nitrogen compounds, and the mixture thereof are useful as the nitrogen source. In addition, sodium chloride, calcium carbonate, magnesium sulfate, iron sulfate, zinc sulfate and various vitamins can be used for the promotion and regulation of the growth of the microorganism. If required, silicone, vegetable oil and synthetic defoaming agents are used in the culture medium to prevent from foaming.

*Streptomyces halstedii* No. 3002-14 strain may be well preserved by lyophilization and by repeated transplantation through a slant agar culture.

Leucanicidin may be accumulated in the cells of the strain as incubated in a culture medium for the productive fermentation and isolated therefrom in the following way; A seed culture medium placed in a shaking culture flask containing a liquid culture medium comprising the above-mentioned nutrients suitable for the seed cultivation of *Streptomyces halstedii* No. 3002-14 is inoculated with a loopful amount of a slant agar culture of *Streptomyces halstedii* No. 3002-14 strain, and the seed cultivation is carried out at 25°~30° C. for 2 to 5 days. The seed cultivation may be repeated depending on the scale required of the productive cultivation in order to provide the seed culture in a large quantity sufficient for the productive fermentation.

For the production of leucanicidin on a large scale, the culture medium having the above-mentioned composition of nutrients in a fermentation tank is inoculated with an amount of the seed culture prepared as above, and agitated at a temperature of 20° to 35° C., preferably at 25° to 30° C. for 2~5 days while sterile air being passed therethrough. After the completion of fermentation, the mycelium cake or the cell is separated from the fermentation broth by centrifugation or filtration techniques, washed with a water-miscible organic solvent such as acetone, methanol or with a mixture of water and a water-miscible solvent such as acetone and methanol, whereby the active substance is extracted into the solvent. The mixed solvent of water and a water-miscible organic solvent for the extraction of the compound of this invention may preferably contain the organic solvent in a range of 50 to 70% by volume. If necessary, the extraction procedure may be repeated several times. The extract thus obtained containing leucanicidin is concentrated under reduced pressure. The resulting oily material containing leucanicidin is admixed with a water-immiscible solvent such as chloroform, ethyl acetate, to transfer leucanicidin from the aqueous layer into the organic solvent layer. The organic solvent layer may be washed with an aqueous solution of a salt such as saturated aqueous solution of sodium chloride, whereby hydrophilic impurities are effectively removed. The solvent layer thus obtained may be treated with sodium sulfate for dehydration, and then concentrated under reduced pressure, affording a crude product containing leucanicidin.

For further purification of leucanicidin, ordinary purification techniques for lipophilic low-molecular weight compounds may be employed. For this purpose, there may be used chromatographic techniques on various kinds of adsorbents. The examples of such adsorbents may be ordinary carriers such as silica gel; alumina; non-ionic, macroporous resin and the like. It is preferred to use silica gel for purification of leucanicidin. A mixed solvent of benzene and ethyl acetate is preferably used as the eluent in this chromatography. The fractions containing mainly leucanicidin may be detected by thin-layer chromatography, and the active fractions are collected and combined. The combined fractions are concentrated under reduced pressure, whereby an oil comprising leucanicidin is obtained. The resulting oil is dissolved in a small volume of chloroform and then added with a volume of n-hexane to precipitate leucanicidin as colorless crystals. The leucanicidin thus obtained shows the physico-chemical properties described hereinbefore.

The biological activity of leucanicidin according to this invention is now illustrated, with showing that leucanicidin exhibits an insecticidal activity against larvae of armyworm (*Leucania separata*). The insecticidal test was carried out as described below.

TEST

Basic diet mixture comprising powdered kidney bean (30 g), bran (30 g), chlorella (30 g), "Ebios" (a trade name of dried yeast powder) (10 g), cellulose powder (20 g), ascorbic acid (4 g), p-hydroxybenzoic acid (0.3 g), sodium propionate (0.3 g), sorbic acid (0.3 g) and agar (7.5 g) was prepared.

A solution of leucanicidin in chloroform was added to the basic diet mixture at such a dose that the diet finally contains leucanicidin at a particular concentration, and the diet mixture containing the leucanicidin solution in chloroform was then allowed to stand under reduced pressure to remove chloroform therefrom by evaporation. Distilled water (350 ml) was added to the whole diet mixture (132.4 g) thus prepared, which was then sterillized in an autoclave at 110° C. for 30 minutes. The diets containing leucanicidin at different particular concentrations were thus prepared. The diet (3.6 g) was placed into a 30 ml.-Erlenmeyer flask, under sterile conditions, and 3 larvae (3rd-instar) of *Leucania separata* which had been incubated under sterile conditions were introduced into the flask while keeping the sterile conditions. The larvae of *Leucania separata* in the flask were fed under the same conditions as those for the previous incubation of the larvae (namely, at temperature of 25° C., at humidity of 50~60%, L-16, D-8). The test was conducted with two replications for each particular concentration of leucanicidin in the diet.

From the test results obtained, it was found that all the test larvae in the flask died in 4 days at the concentration of 20 ppm. of leucanicidin in the diet mixture and that the growth of the test larvae was remarkably inhibited at the concentration of 10 ppm. of leucanicidin in the diet mixture. It is evident therefore that leucanicidin is an insecticide useful for killing or controlling harmful insects such as *Leucania separata*.

This invention, therefore, also provides an insecticide which comprises leucanicidin as active ingredient, in association with liquid or solid carrier for the active ingredient.

EXAMPLE 1

A loopful amount of a slant culture of *Streptomyces halstedii* No. 3002-14 strain (FERM BP-493) was inoculated to a culture medium (100 ml.) comprising 1% malt extract, 0.4% yeast extract, 0.4% glucose, 1% $CaCO_3$, adjusted to pH 7.3 which had been placed in every Erlenmeyer flask of 500 ml capacity and had been sterilized. The incubation was conducted for consecutive 48 hours at 26.5° C. on a reciprocal shaker, whereby a seed culture was prepared for ready to be used in the productive cultivation of said strain. The seed culture thus prepared was added, at an inoculum size of 2 vol. %, to the sterilized culture medium which had the same composition as the culture medium for the seed culture and which had been placed in 100 ml portions in 100 Erlenmeyer flasks each of 500 ml capacity. The productive fermentation was conducted for consecutive 96 hours at 26.5° C. on a reciprocal shaker.

The culture broth obtained was filtered with a filter aid (Cellite) to separate the mycelia. To the mycelia cake was added 2 l of acetone, and the whole mixture was stirred for a while, and then the mixture was allowed to stand for 20 hours to effect the extraction of the active substance (leucanicidin). The mixture was filtered to provide the extract which was concentrated under reduced pressure. The residue obtained was extracted with chloroform. The chloroform layer separated was concentrated to obtain an oily material (1.4 g). The oily material was chromatographed on a column of a silica gel (Silicar CC-7, a product of Mallinckrodt Co.), which was eluted gradiently with a solvent system of benzeneethyl acetate (80:20~50:50 by volume). The fractions containing leucanicidin were collected and evaporated under reduced pressure, whereby an oil comprising leucanicidin was obtained. The oil was dissolved in chloroform and added with n-hexane to give white needles of leucanicidin (50 mg) which showed m.p. of 130°-132° C.

What we claim is:

1. A process for the production of leucanicidin, which comprises cultivating *Streptomyces halstedii* No. 3002-14 FERM BP-493 in an aqueous nutrient medium containing assimilable sources of carbon, nitrogen and inorganic substances, and recovering leucanicidin therefrom.

* * * * *